(12) United States Patent
Ma et al.

(10) Patent No.: US 11,103,565 B2
(45) Date of Patent: *Aug. 31, 2021

(54) SITE-SPECIFIC POLYETHYLENE GLYCOLYLATED (PEGYLATED) ASPARAGINASE, PREPARATION METHOD THEREFOR AND USE THEREOF

(71) Applicants: ZONHON BIOPHARMA INSTITUTE INC., Changzhou (CN); GENSUN INSTITUTE OF BIOMEDICINE CO., LTD., Changzhou (CN)

(72) Inventors: Bruce Yong Ma, Changzhou (CN); Jun Wang, Changzhou (CN); He Wang, Changzhou (CN); Chunlin Xu, Changzhou (CN); Yifei Chen, Changzhou (CN); Yaofang Wang, Changzhou (CN)

(73) Assignees: ZONHON BIOPHARMA INSTITUTE INC., Changzhou (CN); GENSUN INSTITUTE OF BIOMEDICINE CO., LTD., Changzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/746,264

(22) Filed: Jan. 17, 2020

(65) Prior Publication Data

US 2020/0222515 A1 Jul. 16, 2020

Related U.S. Application Data

(63) Continuation of application No. 15/522,445, filed as application No. PCT/CN2015/072167 on Feb. 3, 2015, now Pat. No. 10,537,620.

(30) Foreign Application Priority Data

Dec. 29, 2014 (CN) .......................... 201410837456.3

(51) Int. Cl.
*A61K 38/50* (2006.01)
*A61K 9/19* (2006.01)
*A61K 47/60* (2017.01)
*C12N 9/82* (2006.01)
*A61K 9/00* (2006.01)
*C12N 9/96* (2006.01)
*A61P 35/02* (2006.01)

(52) U.S. Cl.
CPC ............ *A61K 38/50* (2013.01); *A61K 9/0019* (2013.01); *A61K 9/19* (2013.01); *A61K 47/60* (2017.08); *A61P 35/02* (2018.01); *C12N 9/82* (2013.01); *C12N 9/96* (2013.01); *C12Y 305/01001* (2013.01)

(58) Field of Classification Search
None
See application file for complete search history.

(56) References Cited

U.S. PATENT DOCUMENTS

| 4,670,417 | A | 6/1987 | Iwasaki et al. | |
|---|---|---|---|---|
| 10,537,620 | B2 * | 1/2020 | Ma ........................ | A61K 38/50 |
| 2012/0129766 | A1 | 5/2012 | Boettcher et al. | |
| 2017/0043028 | A1 | 2/2017 | Ma et al. | |
| 2017/0049864 | A1 | 2/2017 | Ma et al. | |

FOREIGN PATENT DOCUMENTS

| CN | 101082043 A | 12/2007 |
|---|---|---|
| CN | 101484181 A | 7/2009 |
| CN | 101586099 A | 11/2009 |
| CN | 200810112025.5 | 11/2009 |
| CN | 102573917 A | 7/2012 |
| CN | 104046600 A | 9/2014 |
| CN | 104073482 A | 10/2014 |
| WO | 2009009716 A1 | 1/2009 |

OTHER PUBLICATIONS

Qizhong Fu, Preparation, purification, and identification studies of N-terminal PEG-L-ASP, Master thesis, CDMD (Master), Medicine and hygiene sciences, No. 6, May 15, 2007, with an English abstract. (64 pages).
International Search Report and Written Opinion dated Aug. 31, 2015, by the International Bureau of WIPO, in corresponding International Patent Application No. PCT/CN2015/072167. and an English translation of the International Search Report. (13 pages).
International Preliminary Report on Patentability dated Jul. 4, 2017, by the International Bureau of WIPO, in corresponding International Patent Application No. PCT/CN2015/072167. (4 pages).
Qizhong Fu; "Preparation, Purification, Identification and Research of N-Terminal of PEG-L-ASP," CDMD (Master) Medicine/Hygiene and Science, No. 6; May 15, 2007 (May 15, 2007) p. 18, the first paragraph, p. 37, the first and second paragraphs.
Francesco M. Veronese, et al., "Branched and Linear Poly (Ethylene Glycol): Influence of the Polymer Structure on Enzymological, Pharmacokinetic, and Immunological Properties of Protein Conjugates" Journal of Bioctive and Compatible Polymers; vol. 12; No. 7; Jul. 31, 19997 (Jul. 31, 1197) the abstract, and p. 197, the third paragraph.
CN 101484181 A_ Abstract English Translation, Jul. 15, 2009.
CN 104046600 A_ Abstract English Translation, Sep. 17, 2014.
CN 101082043 _ Abstract English Translation, Dec. 5, 2007.
CN 102573917 A1 _Abstract English Translation, Jul. 11, 2012.
CN 101586099 A _ Abstract English Translation, Nov. 25, 2009.
Qiao Guo, et al. "Studies on the Recombinant Human Asparaginase Modified with Polyethylene Glycol" Biotechnology 127 (2007) 657-669; Available online at www.sciencedirect.com.

(Continued)

*Primary Examiner* — David Steadman
(74) *Attorney, Agent, or Firm* — Buchanan Ingersoll & Rooney PC

(57) ABSTRACT

The present application discloses a PEGylated asparaginase and use thereof. In this application, the polyethylene glycol (PEG) is coupled to the N-terminal amino of 1 or 2 subunits of L-asparaginase, and the molecular weight of the PEG is 30-40 KDa. The PEG is preferably branched and has an aldehyde serving as an activating group. The PEGylated asparaginase is useful in the preparation of anti-tumor drugs.

10 Claims, 7 Drawing Sheets

Specification includes a Sequence Listing.

(56) References Cited

OTHER PUBLICATIONS

Georgia A. Kotzia et al.; "L-Asparaginase from Ervinia Chrysanthemi 3937: Cloning, expression and characterization"; Journal of Biotechnology 127 (2007) 657-669; Available online at www.sciencedirect.com.

Lina Zhang and Daohua Gong; "Toxic Side Effect in Treatment of Childhood Acute Lymphocytic Leukemia with L-Asparaginase"; Jiangsu Medical Journal; vol. 31; No. 5; 392, May 31, 2005.

Ningling Wang and Zhizhang Liu et al., "Toxic Side Effect in Treatment of Childhood Leukemia with L-Asparaginase and Control Thereof"; Journal of China Pediatric Blood; Oct. 3, 2005; 133.

Abraham Abuchowski, et al., "Alteration of Immunological Properties of Bovine Serum Albumin by Covalent Attachment of Polyethylene Glycol"; The Journal of Biological Chemistry 1977; vol. 252; No. 11; Issue of Jun. 10; pp. 2578-2581.

Yin-Jue Wang, et al.; "PEGylation Markedly Enhances the in vivo Potency of Recombinant Human Non-Glycosylated Erythropietin: A Comparison with Glycoslated Erythropoietin"; Journal of Controlled Release 145 (2010) 306-313; www.elsevier.com/locate/jconrel.

Pascal Bailon et al.; "Rational Design of a Potent, Long-Lasting Form of Interferon: A 40 kDa Branched Polyethylene Glycol-Conjugated Interferon α-2a for the Treatment of Hepatitis C"; Bioconjugate Chem.; 2001; 12; pp. 195-202.

Shaoping Chi and Bochu Wang; "Primary Study on the Modification of L-ASP with mPEG"; Pharmaceutical Biotechnology; Mar. 16, 2003; 212-216.

JenKem Y-AALD, Dec. 24, 2014, 3 pages (Year: 2014).

JenKem Y-PALD, Dec. 28, 2014, 3 pages (Year: 2014).

Wang et al., "A PEGylation Technology of L-Asparaginase with Monomethoxy Polyethylene Glycol-Propionaldehyde", Z. Naturforsch C. 67:312-318, 2012 (Year: 2012).

Machine Translation of CN 101586099 A, 5 pages, May 20, 2019 (Year: 2019).

\* cited by examiner

SITE-SPECIFIC POLYETHYLENE GLYCOLYLATED (PEGYLATED) ASPARAGINASE, PREPARATION METHOD THEREFOR AND USE THEREOF

RELATED APPLICATION INFORMATION

This application is a continuation application of U.S. patent application Ser. No. 15/522,445 filed on 27 Apr. 2017, now U.S. Pat. No. 10,537,620, which in turn is a 371 of International Application PCT/CN2015/072167 filed on 3 Feb. 2015, which claims priority from Chinese Application No. 201410837456.3 filed on 29 Dec. 2014, the disclosures of all of which are incorporated in their entirety by reference herein.

REFERENCE TO SEQUENCE LISTING SUBMITTED VIA EFS-WEB

This application includes an electronically submitted sequence listing in .txt format. The .txt file contains a sequence listing entitled "2017-09-11 U 019842-1 ST25.txt" created on Sep. 11, 2017 and is 3,604 bytes in size. The sequence listing contained in this .txt file is part of the specification and is hereby incorporated by reference herein in its entirety.

FIELD OF THE INVENTION

The present invention relates to polyethylene glycolylated (PEGylated) protein drugs, and particularly to a PEGylated asparaginase, a preparation method therefor, and use thereof in the preparation of drugs and in clinical treatment.

DESCRIPTION OF RELATED ART

Asparaginase (ASP) is a protein having L-asparagine aminohydrolase activity (generally referred to as L-asparaginase, or asparaginase). An active form of ASP is a homologous tetramer formed of 4 subunits, in which each subunit comprises 326 amino acids. L-asparaginase is effective in the treatment of acute lymphoblastic leukemia (ALL) in children or adults. In recent years, the drugs containing L-asparaginase are used in combination with chemotherapy to treat NK/T cell lymphoma, and a good therapeutic effect is achieved. The NK/T cell lymphoma is a special non-Hodgkin lymphoma, which is frequently found in Asia and Latin America, and the incidence is relatively high in China. Depending on the tumor site, the NK/T cell lymphoma may include nasal NK/T cell lymphoma and non-nasal NK/T cell lymphoma. Moreover, the L-asparaginase is also used to treat Hodgkin's disease, acute myeloid leukemia, acute myelomonocytic leukemia, chronic lymphocytic leukemia, lymphosarcoma, reticulum cell sarcoma and melanotic sarcoma (Kotzia and labrou, J. Biotechnol. 127 (2007) 657-669).

The L-asparaginase is initially purified from several organisms, including *E. coli* and *Erwinia carotovora*. For the mammalians, the L-asparaginase is found only in slightly more than trace amount in guinea pig (superfamily Cavioidea) and some platyrrhinians (New World monkey). However, the L-asparaginase is a foreign protein having a high immunogenicity for human since it is derived from exogenous organisms, and limited in use in clinic due to the commonly occurred progressive immune reaction and systemic anaphylaxis in clinic (ZHANG Lina, and GONG Daohua. Jiangsu Medical Journal. Toxic side effect in treatment of childhood acute lymphocytic leukemia with L-Asparaginase. 2005, 31(5):392; and WANG Ningling, and LIU Zhizhang, et al. Toxic side effect in treatment of childhood leukemia with L-Asparaginase and control thereof. Journal of China Pediatric Blood, 2005, 10(3):133). Moreover, the naturally occurring L-asparaginase molecule has a short half-life in human and has to be administered at a short interval, causing reduced patient compliance.

In view of these disadvantages, the drug is modified in various aspects in the prior art. For example, (1) for the patients susceptible to *E. coli* derived L-asparaginase, *Erwinia carotovora* derived enzyme is used in place of the *E. coli* derived L-asparaginase; (2) the dosage form of L-asparaginase is changed, which is, for example, prepared into a L-asparaginase-lipidosome, and other forms; (3) the antigenic site of *E. coli* derived L-asparaginase is mutated by changing the structure through protein engineering to reduce the immunogenicity; and (4) chemical modifications are made to the structure of L-asparaginase. PEGylation is one of the chemical modifications.

Polyethylene glycol (PEG) is an uncharged linear polymer that can freely coil in a solution, is non-toxic and weakly antigenic, and has a good biocompatibility. Covalent modification of a protein with PEG (PEGylation) can increase the in-vivo circulation half-life, reduce the antigenicity, enhance the solubility, and alter the biodistribution in human of the protein. Since the initial report about the PEGylation by Abuchowski, Davis et al (J. Biol. Chem. 1977, 252:3578-3581.) in 1977, PEGylation has found wide use in the fields of biomedicines and biotechnologies and used extensively in the modification of proteins and polypeptides. At present, the technology for protein PEGylation has become one of the most effective ways to reduce the immunogenicity and improve the pharmacokinetic/pharmacodynamic properties of protein drugs, and is approved by FDA for use with medicines, food, and cosmetics.

After decades of development, the PEGylation technology is mature at present. However, there are no general-purpose PEG modifiers and modification methods available for modifying all the protein drugs. The protein structure, the molecular weight and shape of PEG used, and the site to be modified have a high influence on the bioactivity and therapeutical efficacy of the PEGylated proteins. For the modification of a particular drug, the PEG modifier is an important factor affecting the physical and chemical properties, in-vivo and in-vitro bioactivity, pharmacokinetics, pharmacodynamics, and clinical manifestations of the modified products. Therefore, the choice of the modifier (the type and molecular weight of the modifier) and the control over the modification play an important role in the PEGylation technology. The pharmacokinetic behavior of a natural protein cannot be precisely predicted by the analysis of protein structure, and the prediction for the pharmacokinetic behavior of a PEG conjugate becomes even less feasible after PEG is conjugated to a protein, because numerous new variables such as molecular weight and the type of the modifier are introduced. In this regard, optimum solutions are determined for various protein drugs by selecting different types and different molecular weights of modifiers and by detection of physical and chemical properties and evaluation with animal experiments.

For example, in most cases, as compared with unPEGylated original proteins, the activity of the PEGylated protein drugs is reduced, and is generally only 30-40% or even lower of that of the original proteins. For example, PEG-Intron available from the Schering-Plough Corporation is an interferon modified with PEG having a molecular weight of 5000, the activity of which after modification is only 8% of that of the original protein. *E. coli* derived asparaginase is modified by Yoshihiro et al with branched activated PEG (2-O-methoxy poly ethylene glycol-4,6-dichloro-s-triazine) having a molecular weight of 750, 1900, 5000 U. 73 out of all the 92 free amino groups (88 δ-amino groups and 4 α-amino groups) in asparaginase are modified by 5000 u-PEG, by which the enzyme retains 7% of the original activity, and the modified product completely loses the ability to bind to asparaginase-resistant serum. In addition, the protein activity after modification generally decreases much considerably with increasing molecular weight of PEG. For example, the activity of erythropoietin (EPO) modified with PEG having a molecular weight of 20 kDa, 30 kDa, and 40 kDa decreases significantly with increasing molecular weight of PEG (Yin-jue Wang, journal of controlled release, 2010 (145):306-313). Interferon-α-2a is modified by Bailon et al with a branched 40 kDa PEG, and the resultant monoPEGylated product has a long circulation half-life, but retains only 7% of the in-vitro activity (Bailon P, Bioconjugate Chem., 2001, 12:195-202.).

At present, PEGylation of L-Asparaginase is extensively researched. The PEGylated L-asparaginase product Oncaspar (Enzon Inc) became available abroad as early as in 1994, and was approved in 2006 as the first line treatment for ALL in children and adults. However, Oncaspar is modified with succinimidyl succinate-PEG (SS-PEG), and has the disadvantage of non-uniform modified products and large loss in the activity of the modified products, and contains an ester bond that is susceptible to enzymatic hydrolysis or is labile at a slightly basic pH (U.S. Pat. No. 4,670,417), which greatly reduce the in-vitro and in-vivo stability and may cause a high adverse effect. The PEGylated L-asparaginase marketed in China is exclusively "Pegaspargase" manufactured by Hengrui Medicine Co., Ltd., which is a generic drug of Oncaspar, and also suffers from the above problem.

The two products are both randomly modified and thus not uniform, and have a composition comprising L-asparaginase coupled with different number of PEG molecules. Moreover, after random modification, the active site of asparaginase suffers from high steric hindrance, due to the presence of numerous PEGylated sites. Therefore, the activity is considerably lost, and only 60% of the activity of the original protein is retained. Relevant research on N-terminal site-specific modification of asparaginase is reported in literatures and the activity of the modified products is only about 36% of the original protein (CHI Shaoping, WANG Bochu. Primary study on the modification of L-ASP with mPEG). In another Chinese patent relating to N-terminal site-specific modification of asparaginase (Application No. CN200810112025.5), a linear PEG having a molecular weight of 20 KDa is used, and the finally obtained modified product after purification has PEG coupled to the N terminus of one subunit of asparaginase, and to an amino group at the amino acid side chain of the subunit. The modified product retains only about 40% of the biological activity of the original protein, and the activity loss is large. In the above two examples, linear PEG is used for site-specific modification of asparaginase.

SUMMARY OF THE INVENTION

Technical Problem to be Solved

To solve the technical problem existing in the prior art, the present invention provides a site-specific PEGylated asparaginase (ASP) having an increased stability, a reduced immunogenicity, and also high activity, and uniform composition, a preparation method therefor, and use thereof in the preparation of drugs for treating acute lymphoblastic leukemia, non-Hodgkin lymphoma, and other diseases in children or adults.

Further, a first objective of the present invention is to provide a site-specific PEGylated L-asparaginase, in which the PEG is coupled to the N-terminal amino of 1 or 2 subunits of L-asparaginase, has a molecular weight of 30-40 KDa, is branched and has an aldehyde group serving as an activating group.

Preferably, the PEG is coupled to the N-terminal primary amino of 2 subunits of L-asparaginase, and the molecular weight of the PEG is 30 or 40 KDa, is branched and has an activating group which is acetaldehyde, propionaldehyde, butyraldehyde, or valeraldehyde.

The site-specific PEGylated L-asparaginase has a general structural formula below:

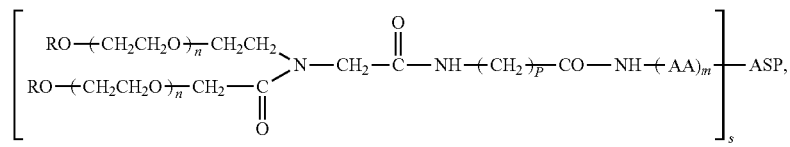

where R is H or a C1-C4 alkyl; n is an integer from 100 to 500, P is an integer from 1 to 4; AA is an N-terminal L-amino acid residue, m is an integer from 0 to 5, and s is 1 or 2.

Preferably, the alkyl is methyl, n is an integer from 320 to 455, P is 2, and m is 0.

A second objective of the present invention is to provide a method for preparing the site-specific PEGylated ASP. The method comprises: Step 1: formulating a 15-20 mg/mL L-asparaginase solution in 40 mM acetic acid-sodium acetate buffer pH 4-6; Step 2: reacting for 12-24 hrs at 4° C. at a molar ratio of L-asparaginase:PEG:reducing agent=1: (4-5):(100-200); and Step 3: purifying by ion exchange chromatography after reaction, to finally obtain monoPEGylated or diPEGylated L-asparaginase.

The PEG preferably has a molecular weight of 40 KDa.

The purified PEGylated L-asparaginase product is preferably a diPEGylated product.

The reducing agent is preferably sodium cyanoborohydride.

A third objective of the present invention is to provide use of the site-specific PEGylated ASP in the preparation of drugs for treating acute lymphoblastic leukemia (ALL), non-Hodgkin lymphoma, and other diseases in children or adults. At present, it is reported in literatures that PEGylated asparaginase is used in combination with chemical therapy for treating NK/T cell lymphoma or acute lymphoblastic leukemia, and a good therapeutic effect is achieved. Therefore, the PEGylated asparaginase prepared through site-specific modification provided in the present invention is also useful in treating NK/T cell lymphoma or acute lymphoblastic leukemia in combination therapy.

A fourth objective of the present invention is to provide a site-specific PEGylated ASP or a pharmaceutically acceptable salt or complex thereof. The complex is a conjugate formed with two or more different substances.

A fifth objective of the present invention is to provide a pharmaceutical composition comprising the site-specific PEGylated ASP or a pharmaceutically acceptable salt or complex thereof, and a pharmaceutically acceptable adjuvant.

The pharmaceutical composition is in the dosage form of a liquid injection or a freeze-dried powder injection.

The pharmaceutically acceptable adjuvant includes a pharmaceutically acceptable carrier and/or excipient.

The site-specific PEGylated L-asparaginase and the pharmaceutical composition thereof are administered by intramuscular, intravenous, or subcutaneous route.

Beneficial Effect

The site-specific PEGylated ASP provided in the present invention has the advantages of obviously extended half-life, stable and uniform structure, and further greatly increased biological activity.

Pegaspargase, Y-PALD-40K-ASP (Mono), Y-PALD-40K-ASP (Di), Y-PALD-30K-ASP (Mono), and Y-PALD-30K-ASP (Di) are analyzed respectively by SEC. As can be seen from the results that after purification, the Y-PALD-40K-ASP (Mono), Y-PALD-40K-ASP (Di), Y-PALD-30K-ASP (Mono), and Y-PALD-30K-ASP (Di) have a purity up to 98% or above, which is slightly higher than the purity of Pegaspargase of 97%. Compared with Pegaspargase, Y-PALD-40K-ASP (Di), and Y-PALD-30K-ASP (Di) have an even higher molecular weight.

Figure 2A:
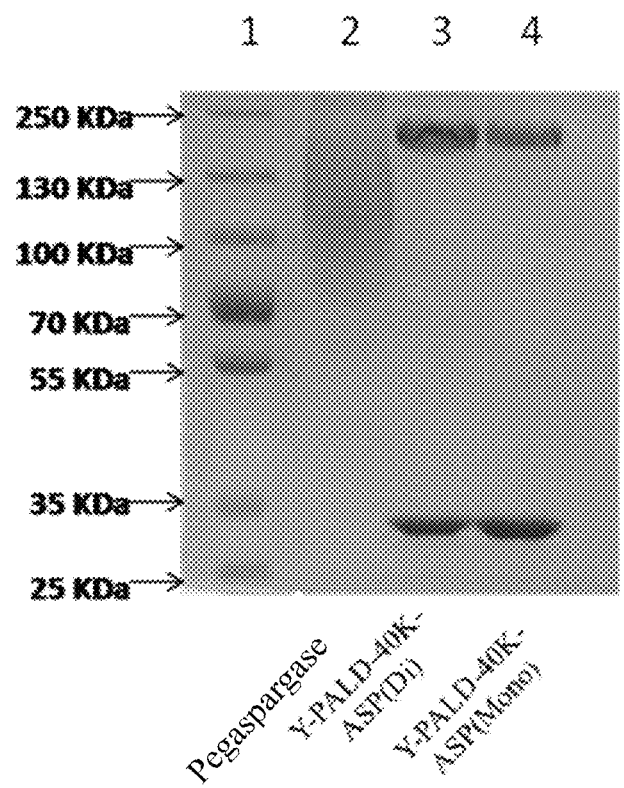
Figure 2B:
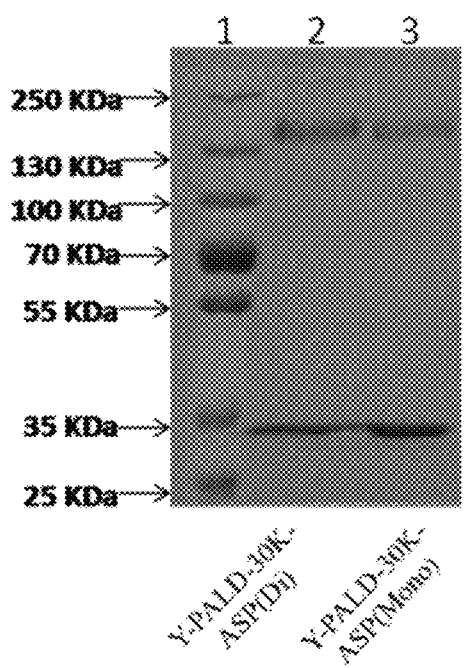

FIGS. 2a and 2b show analysis of various PEG-ASP conjugate by SDS-PAGE.

Pegaspargase, Y-PALD-40K-ASP (Mono), Y-PALD-40K-ASP(Di), Y-PALD-30K-ASP (Mono), and Y-PALD-30K-ASP (Di) are analyzed by reductive SDS-PAGE. In FIG. 2a, the proteins in Lanes 1-4 are a high-molecular-weight Marker, Pegaspargase, Y-PALD-40K-ASP (Mono), and Y-PALD-40K-ASP (Di) respectively. In FIG. 2b, the proteins in Lanes 1-3 are a high-molecular-weight Marker, Y-PALD-30K-ASP (Di), and Y-PALD-30K-ASP (Mono) respectively. Because ASP is a homologous tetramer formed of 4 subunits, depolymerization of the four subunits occurs in a reductive environment. Depending on different degrees of PEGylation, each unit is manifested as a different strip in SDS-PAGE. As shown in FIGS. 2a and 2b, Pegaspargase is manifested as a diffuse strip, indicating a poor protein uniformity. Compared with Pegaspargase, Y-PALD-40K-ASP (Mono) and Y-PALD-40K-ASP (Di) show two distinct strips of modified and unmodified subunit and thus have a high uniformity. Strips of high molecular weight shown in Lanes 3 and 4 in FIG. 2a and Lanes 2 and 3 in FIG. 2b denote PEGylated single subunits of ASP, and strips of small molecular weight denote unPEGylated single subunits of ASP.

Figure 3:
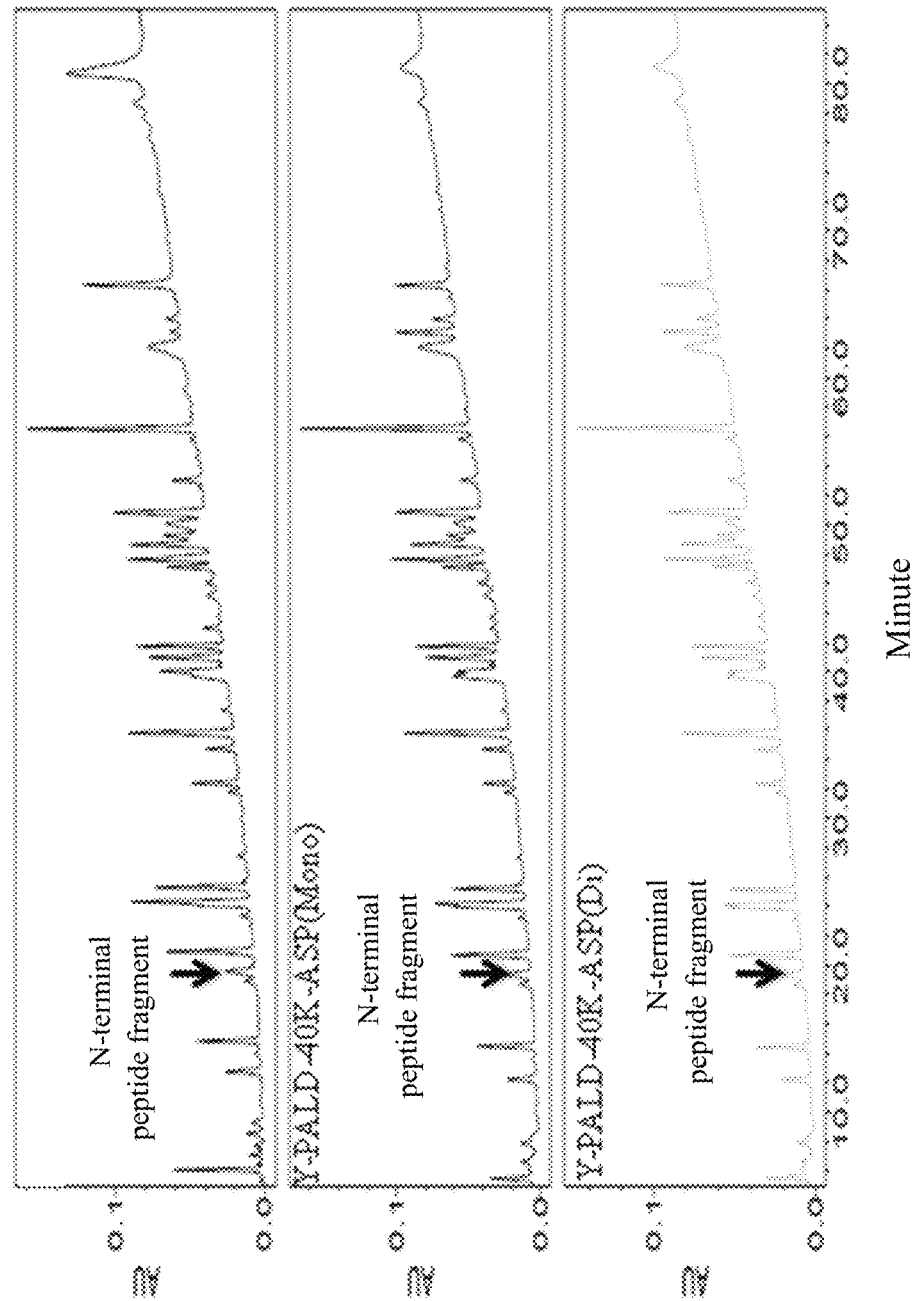

FIG. 3 shows identification of PEGylated sites in PEG-ASP conjugates.

As can be seen from the peptide mapping of the PEG-ASP conjugates and the original protein after trypsinization, for Y-PALD-40K-ASP (Mono) and Y-PALD-40K-ASP (Di), PEGylation occurs at the N terminus of the protein. In Y-PALD-40K-ASP (Mono), only one PEG molecule is coupled to the N terminus of one of the 4 subunits in asparaginase. In Y-PALD-40K-ASP (Di), the N terminus of two of the 4 subunits in asparaginase are coupled with one PEG molecule respectively.

Figure 4:
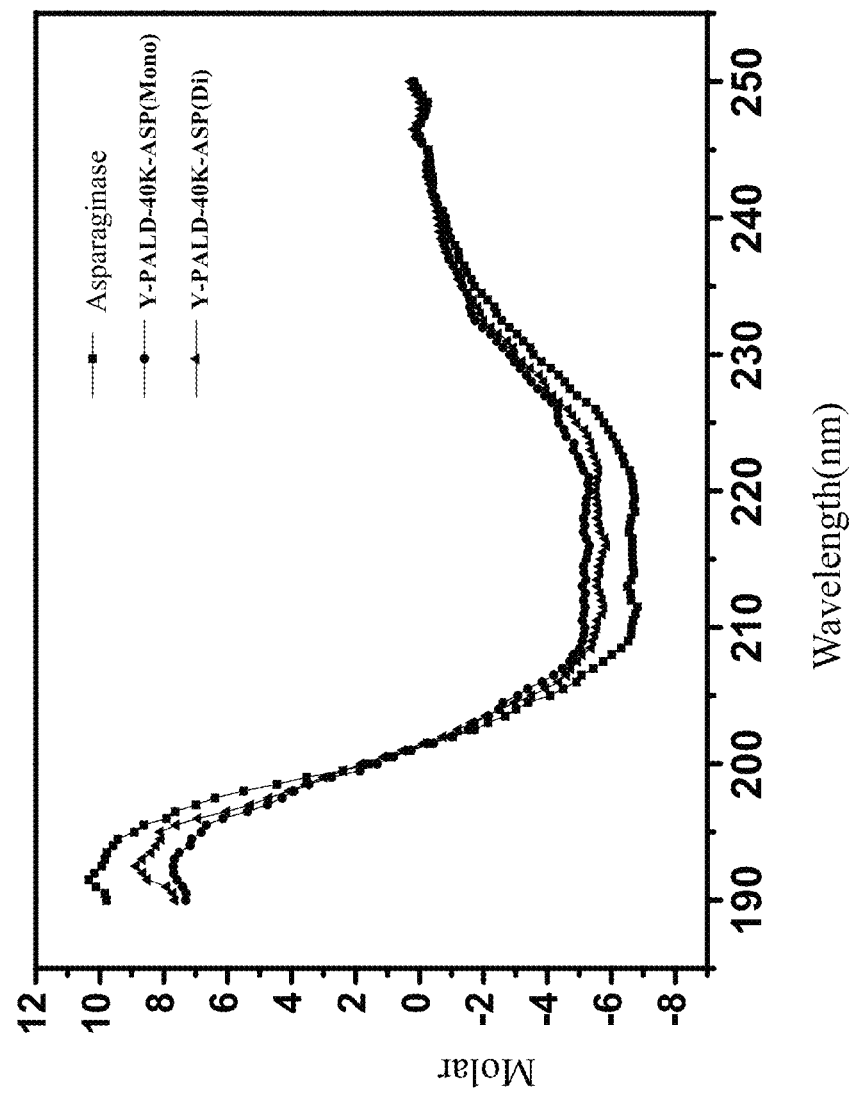

FIG. 4 shows analysis of various PEG-ASP conjugates by circular dichroism spectroscopy.

The structure of asparaginase, Y-PALD-40K-ASP (Mono), and Y-PALD-40K-ASP (Di) is identified by circular dichroism spectroscopy. The result from far-ultraviolet scanning shows that compared with asparaginase, the characteristic circular dichroism spectra of Y-PALD-40K-ASP (Mono) and Y-PALD-40K-ASP (Di) have no obvious changes, and the near-ultraviolet scanning shows the same result. Accordingly, it is considered that after modification with Y-PALD-40K-PEG, no change occurs to the main structure of the protein.

Figure 5:
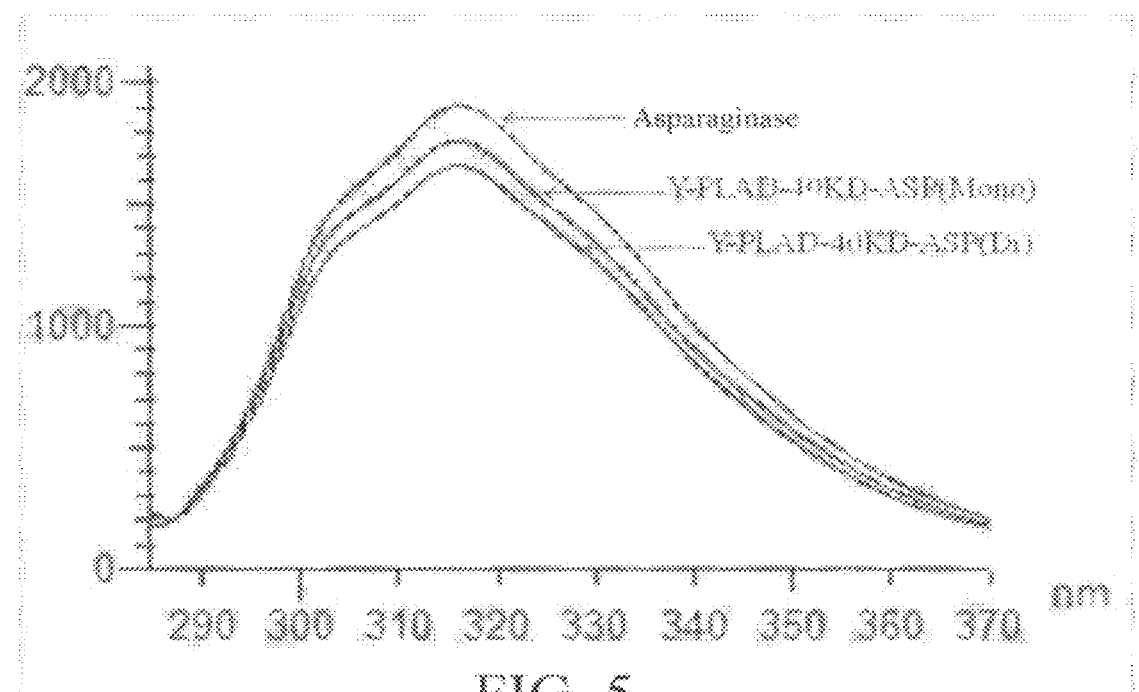

FIG. 5 shows analysis of various PEG-ASP conjugates by fluorescence spectroscopy.

Intrinsic fluorescence spectroscopy is conducted on asparaginase Y-PALD-40K-ASP (Mono), and Y-PALD-40K-ASP (Di) by using a fluorospectrophotometer. The result shows that PEGylation does not change the tertiary structure of asparaginase.

Figure 6A:
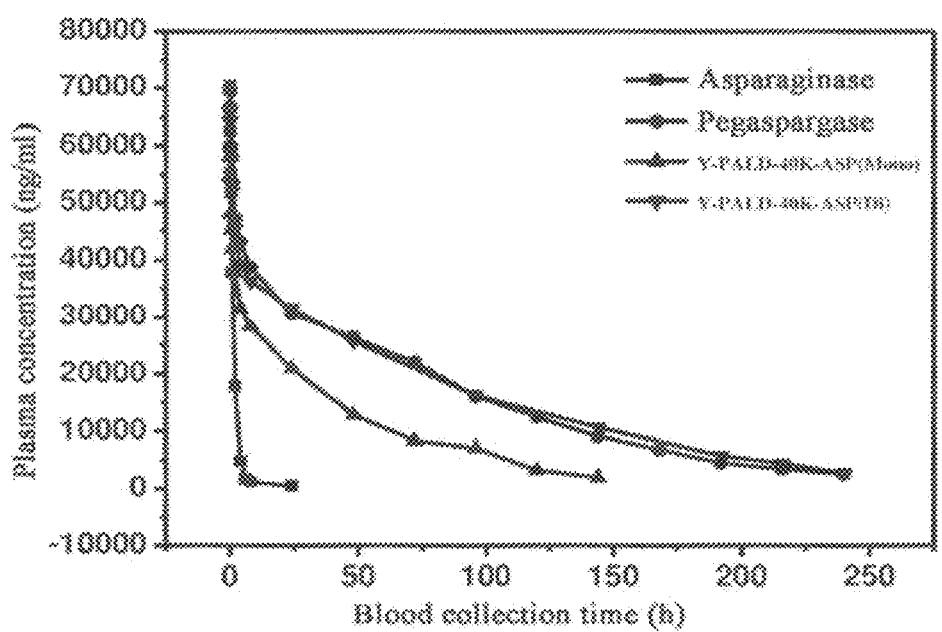
Figure 6B:
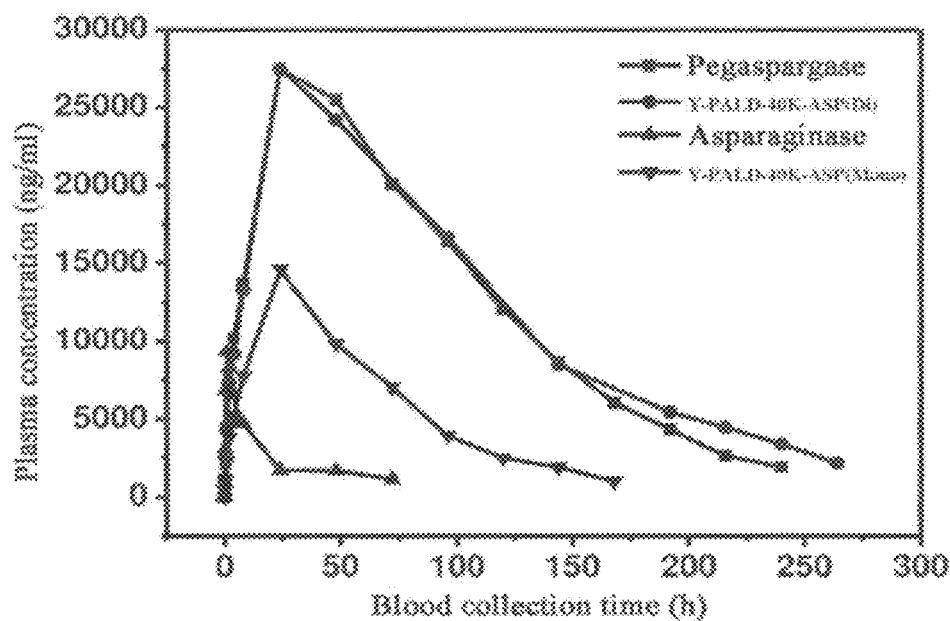

FIGS. 6a and 6b show detection of the pharmacokinetic property of asparaginase and PEG conjugates thereof.

FIG. 6a shows the pharmacokinetic results after intravenous injection, and FIG. 6b shows the pharmacokinetic results after intramuscular injection.

The in-vivo plasma concentration of the PEGylated asparaginase is studied by the $^{125}$I isotope tracing method. It can be seen from the result that compared with asparaginase, both Y-PALD-40K-ASP (Mono) and Y-PALD-40K-ASP (Di) have better pharmacokinetic property, where the Y-PALD-40K-ASP (Di) has a much remarkably improved pharmacokinetic property.

Figure 7:
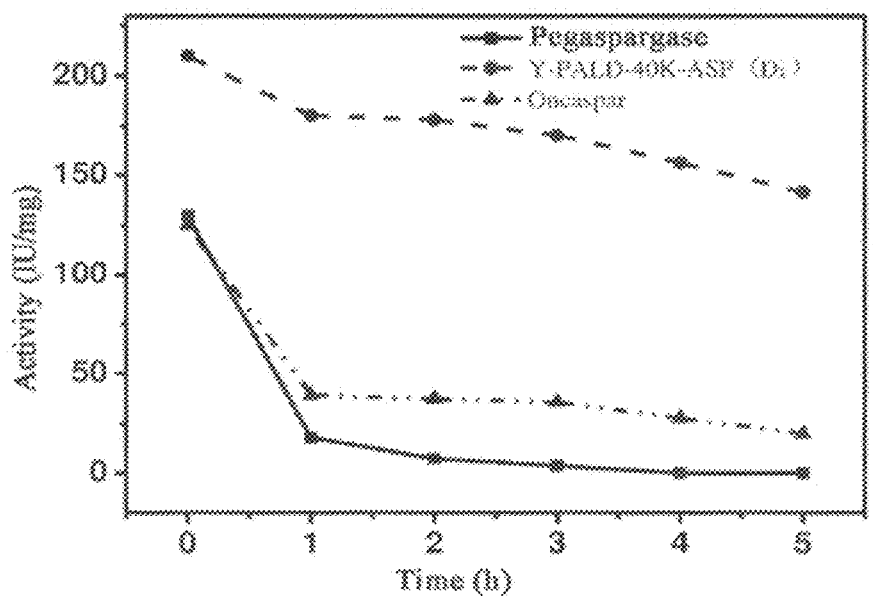

FIG. 7 shows activity tests of various PEG-ASP conjugates after thermal treatment.

Figure 8:
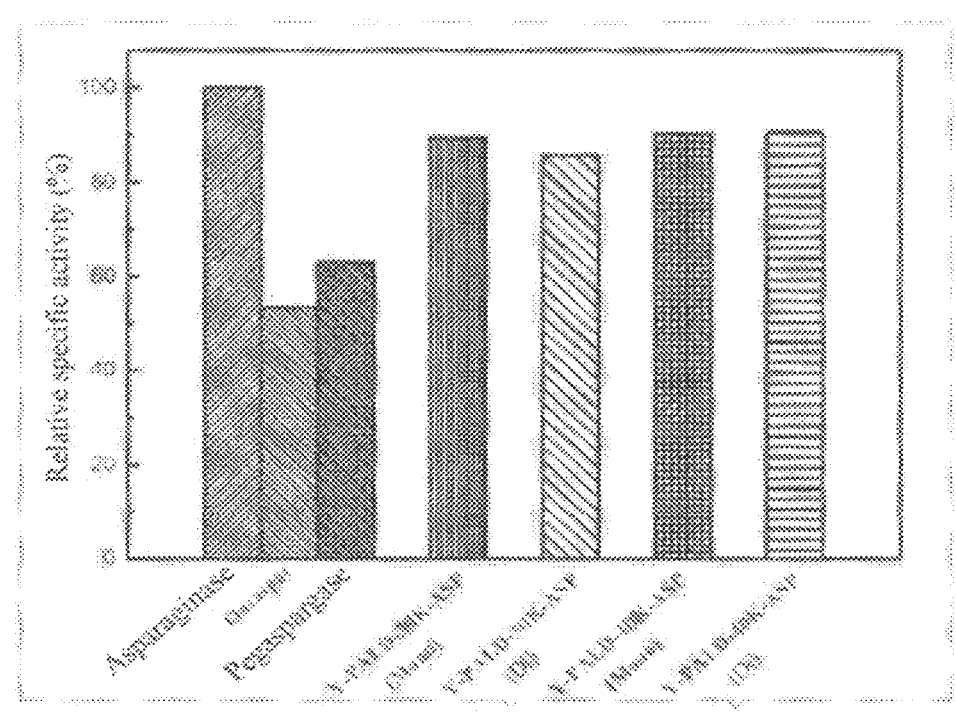

FIG. 8 shows in-vitro enzyme activity tests of various PEG-ASP conjugates.

The in-vitro enzyme activity of asparaginase, Oncaspar, Pegaspargase, Y-PALD-40K-ASP (Mono), Y-PALD-40K-ASP (Di), Y-PALD-30K-ASP (Mono), and Y-PALD-30K-ASP (Di) is detected following the method as described in *Pharmacopoeia of People's Republic of China*. It can be seen from the result that compared with asparaginase, the modified products have different degrees of activity loss after modification. The activity loss is large for Oncaspar and Pegaspargase, and is relatively small for the modified products of the present invention.

DETAILED DESCRIPTION OF THE INVENTION

Definitions

The abbreviations used herein have the following meanings:

PEG: polyethylene glycol; PEG modifier: polyethylene glycol modifier.

Polyethylene glycol (PEG, HO—(CH2CH2O)n-CH2CH2OH) is a linear polymer bearing a hydroxyl group at two ends, which is formed through polymerization of ethylene oxide and composed of repeated oxyethylene, and may be branched, linear or multi armed. PEG is also referred to as poly (ethyleneoxide) (PEO), poly (oxy-ethylene) (POE), or polyoxirane. In general, the term PEG is used when the molecular weight is less than 20,000, and the term PEO is used when the molecular weight is higher. The ordinary PEG has a hydroxyl group respectively at two ends, and methoxy PEG (mPEG) is obtained if the PEG is capped with a methyl group at one end, which is frequently used in PEGylation of proteins.

Polyethylene glycol modifier refers to a functionalized PEG derivative which is activated polyethylene glycol mainly used in the modification of protein and polypeptide drugs, and is also referred to as modifying polyethylene glycol or modifying PEG.

Y-PALD-40K is 40 KDa branched PEG-propionaldehyde, and has a general structural formula of

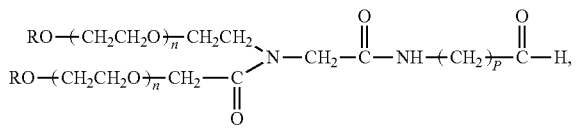

where R is methyl, n is 455, p is 2.

Y-PALD-30K is 30 KDa branched PEG-propionaldehyde, and has a general structural formula of

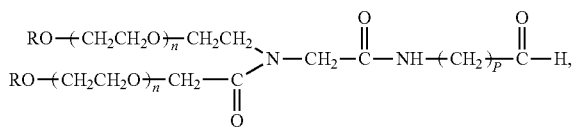

where R is methyl, n is 320, and p is 2.

ASP denotes asparaginase.

As used herein, the term "conjugate" refers to a modified product obtained after PEGylation of asparaginase.

Several modified products obtained after PEGylation of asparaginase are referred to herein as "Y-PALD-40K-ASP (Mono) (a monoPEGylated product obtained after asparaginase is modified with 40K PEG-propionaldehyde and purified, where the PEG is coupled only to the N terminus of one subunit), Y-PALD-40K-ASP (Di) (a diPEGylated product obtained after asparaginase is modified with 40K PEG-propionaldehyde and purified, where the PEG is coupled to the N terminus of two subunits), Y-PALD-30K-ASP (Mono) (a monoPEGylated product obtained after asparaginase is modified with 30K PEG-propionaldehyde and purified, where the PEG is coupled only to the N terminus of one subunit), and Y-PALD-30K-ASP (Di) (a diPEGylated product obtained after asparaginase is modified with 30K PEG-propionaldehyde and purified, where the PEG is coupled to the N terminus of two subunits)", which are collectively referred to as PEG-ASPs, or PEGylated ASP conjugates. Oncaspar is the product name of a reference listed drug.

The PEG modifier used in the present invention preferably includes an aldehyde activated PEG. Specifically, the PEG modifier is propionaldehyde activated PEG.

In the present invention, the modified asparaginase may be of any source. Asparaginase may be extracted without limitation from E. coli, or recombinantly expressed. In a specific conjugate embodiment of the present invention, the asparaginase has a sequence that is at least about 60% identical to that of the protein as shown in SEQ ID NO:1, and more particularly at least about 65%, 70%, 75%, 80%, 85%, 90%, 91%, 92%, 93%, 94%, 95%, 96%, 97%, 98% or 100% identical to that of the protein as shown in SEQ ID NO:1.

In a particular embodiment, the protein is asparaginase derived from E. coli which has the sequence as shown in SEQ ID NO:1.

Example 1: Preparation and Analysis of PEG Conjugate of ASP

Preparation Example 1: Preparation, Purification and Identification of the Site-Specific PEGylated ASP According to the Present Invention 1. Preparation of PEG Conjugate Sample The L-asparaginase (available from Qianhong Biopharma Co., Ltd) was dissolved in a 40 mM acetic acid-sodium acetate buffer (pH 5.0) to formulate a 20 mg/mL solution, and then reacted with Y-PALD-40K (available from Beijing Jiankai science and Technology Co. Ltd.) as a PEG modifier. The reaction was carried out at 4° C. for 12 hrs at a molar ratio of asparaginase:PEG:sodium cyanoborohydride 1:4:200, and then terminated with 1 M glycine. A monoPEGylated product Y-PALD-40K-ASP (Mono) and a diPEGylated product Y-PALD-40K-ASP (Di) were obtained.

2. Purification of PEG Conjugate Sample

Chromatography conditions: Q ion exchange column (available from GE, HiTrap Q HP 5 mL), buffer A: 20 mM Tris-HCl (pH 9.0); buffer B: 1 M NaCl in 20 mM Tris-HCl (pH 9.0), flow rate: 2.5 mL/min; and detection wavelength 280 nm.

Sample loading: The modified product was adjusted to pH 9.0 with a 0.5 M NaOH solution, and bound to the Q ion exchange column.

Equilibrium: The column was washed with 5 column volumes of the buffer A.

Elution: The sample was eluted for 20 min with 10 column volumes of 0-50% of the buffer B, and the sample was collected fractionwise.

2. Detection of PEG Conjugate Sample 2.1 Detection by Chromatography:

Chromatography conditions: HPLC (Waters, e2695 HPLC), Superdex 200 10/300GL (available from GE), mobile phase: 0.1 M Na$_2$SO$_4$ in PBS (pH7.4), flow rate: 0.4 mL/min, detection wavelength: 280 nm, injection volume: 50 μL, and detection time: 60 min.

Figure 1A:
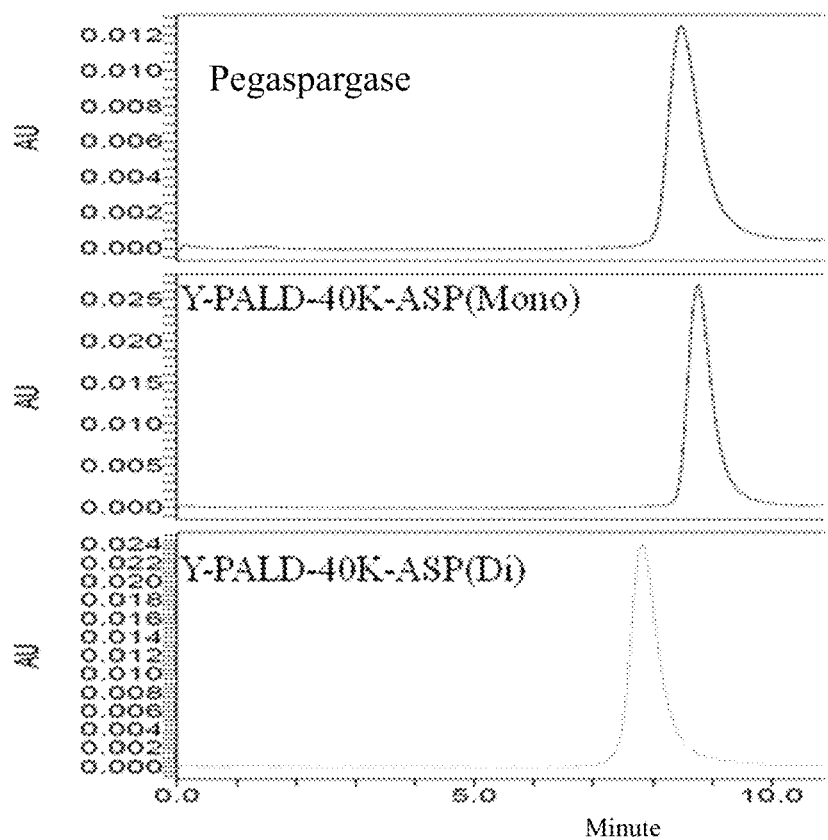
FIGS. 1a and 1b show analysis of various PEG-ASP conjugates by HPLC.

The analysis result is as shown in FIG. 1a. It can be seen from FIG. 1a that the purities of the prepared products Y-PALD-40K-ASP (Mono) and Y-PALD-40K-ASP (Di) are both higher than 98%. Moreover, the molecular weight of the PEGylated product Y-PALD-40K-ASP (Di) is also higher than that of Pegaspargase (available from Jiangsu Hengrui Pharmaceutical Co., Limited).

2.2 Detection by Electrophoresis

The stacking gel was 8%, and the resolving gel was 7%. The stacking gel buffer was 0.5 M Tris-HCl buffer (pH 6.8) and the resolving gel buffer was 1.5 mol/L Tris-HCl buffer (pH 8.8). 10 μg of the protein sample was mixed with the sample buffer of equal volume, boiled for 5 min at 100° C., then loaded and run, and stained with Coomassie brilliant blue (available from Sinopharm Group) after electrophoresis. The identification result is as shown in FIG. 2a.

In Preparation Example 2, the PEG is Y-PALD-30K, the specific parameters and yield are shown in Table 1, and the process steps and parameters not mentioned in Table 1 are the same as those in Preparation Example 1.

TABLE 1

| Experimental condition | Corresponding experiment parameter |
|---|---|
| pH | 5.0 |
| Modifier | Y-PALD-30K |
| Molar ratio (protein:PEG:reducing agent) | 1:5:100 |
| Reaction temperature | 4° C. |
| Reaction time (hr) | 24 |
| Protein concentration (mg/mL) | 15 |

Figure 1B:
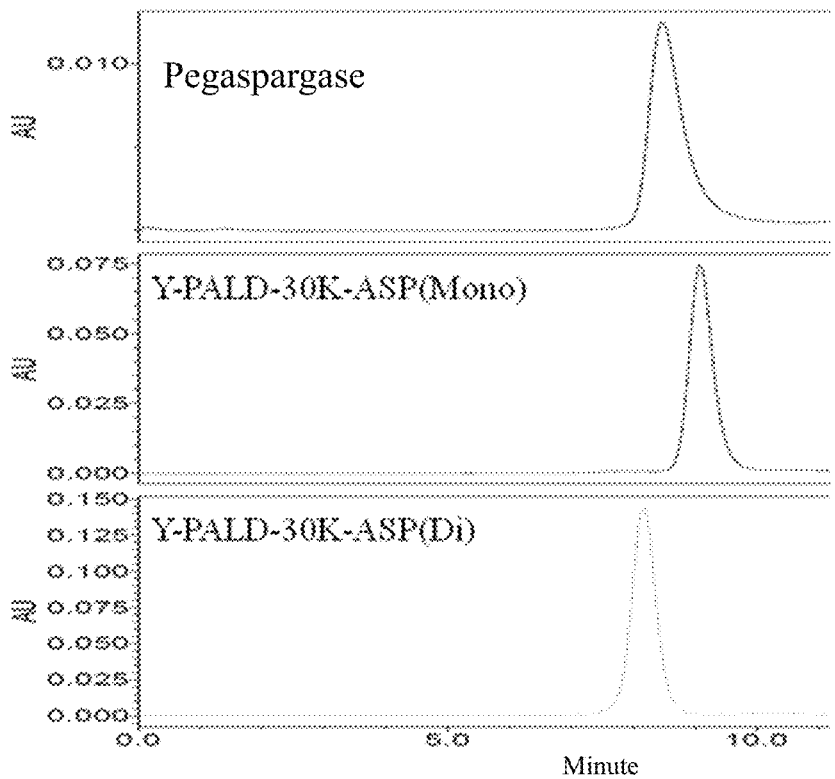

The PEGylated products obtained in Preparation Example 2 were also identified by chromatography and electrophoresis. The results are shown in FIGS. 1b and 2b.

There are no significant difference between the activity and purity of the monoPEGylated and diPEGylated product obtained in Preparation Example 2 and in Preparation Example 1. The purities of Y-PALD-30K-ASP (Mono) and Y-PALD-30K-ASP (Di) are both higher than 98%.

It can be seen from FIGS. 2a and 2b that the PEGylated products Y-PALD-40K-ASP (Mono), Y-PALD-40K-ASP (Di), Y-PALD-30K-ASP (Mono), and Y-PALD-30K-ASP (Di) have very uniform electrophoresis strips. Compared with the similar product—egaspargase (manufactured by Jiangsu Hengrui Pharmaceutical Co., Limited) available in domestic market, the uniformity is greatly increased.

Lanes 3 and 4 in FIG. 2a both show two uniform strips. A first strip in Lanes 3 and 4 corresponds to a molecular weight of about 200 KDa. The PEG molecular binds a large number of water molecular in the solution, and thus the apparent molecular weight is about 4 times of the theoretical molecular weight. Therefore, it can be preliminarily determined that this strip is a subunit of asparaginase having one PEG molecule coupled thereto. A second strip corresponds to a molecular weight of about 34 KDa, which is consistent with the molecular weight of a single subunit of asparaginase. Therefore, it can be preliminarily determined that the second strip is a single subunit of asparaginase having no PEG molecule coupled thereto. It can be seen from the analysis result by software that the ratio of the contents in the first and second strip of Lane 3 is 1:1, suggesting that the PEGylated product has two subunits coupled with PEG, and the other two subunits coupled no PEG, and thus is determined to be a diPEGylated product. Similarly, it can be seen from the analysis result by software with respect to Lane 4 that the ratio of the contents in the first and second strip of Lane 4 is 1:3, suggesting that the PEGylated product has only one subunit coupled with PEG and the other three subunits coupled no PEG, and thus is determined to be a monoPEGylated product. The results are as expected. The commercially available product Pegaspargase in Lane 2 shows a diffuse strip, because Pegaspargase is randomly modified and different number of PEG molecules are coupled to each subunit of asparaginase in the finally PEGylated product, so a diffuse strip is exhibited during electrophoresis. From the perspective of product uniformity, the site-specific PEGylated product prepared in the present invention is advantageous due to the high uniformity. Compared with FIG. 2a, similar results are obtained in FIG. 2b, with the difference that since the PEG used has a molecular weight of 30 KDa, a first strip in Lanes 2 and 3 in FIG. 2b corresponds to a molecular weight of about 150 KDa, which is slightly lower than that of the product modified with PEG having a molecular weight of 40 KDa.

Example 2: Identification of PEGylated Sites in PEG-ASP Conjugates

To determine the PEGylated sites in PEG-ASP conjugates, the PEG-ASP conjugate was trypsinized, and the peptide mapping was compared with that of the original protein after trypsinization. The PEGylated site could be determined by comparing the difference between the peptide fragments of the original protein and the PEGylated product. The specific experimental steps were as follows. 100 µl of 0.5 mg/mL sample was added to 0.9 µl of 1 mg/mL trypsin solution, and reacted at 37° C. for 5 hrs. After reaction, 10 wt % TFA was added to terminate the reaction. The trypsinized product was analyzed by chromatography on reversed phase C18 column (available from Waters), in which the mobile phases included mobile phase A: $H_2O$+0.1 wt % TFA, and mobile phase B: acetonitrile+0.1 wt % TFA. The sample loaded was 80 µL, the flow rate was 0.5 mL/min, and the running time was 120 min. The condition for gradient elution was gradient from 5 to 60 wt % B over 0-100 min.

The comparison result of peptide fragment is shown in FIG. 3. It can be seen from FIG. 3 that compared with the original protein, the N-terminal peptide fragments of the PEG-ASP conjugates Y-PALD-40K-ASP (Mono) and Y-PALD-40K-ASP (Di) have an peak area reduced by 25% and 50% respectively, indicating that the PEG has definitely been coupled to the N-terminal amino acid of ASP. This is as expected. Y-PALD-40K-ASP (Mono) is a monoPEGylated product, in which only one PEG molecule is coupled to one subunit of asparaginase, and the other 3 subunits have no PEG molecules coupled thereto. Therefore, after the conjugate is trypsinized, only the peak of the N-terminal peptide fragment of the one subunit is shifted and no changes occur to the peaks of the N-terminal peptide fragments of the other three subunits since no PEG molecules are coupled thereto, compared with the original protein. Accordingly, the peak area of the N-terminal peptide fragments is finally reduced only by 25%. For the diPEGylated product Y-PALD-40K-ASP (Di), each asparaginase molecule has two subunits coupled with a PEG molecule, and thus the peak area of the N-terminal peptide fragments is finally reduced by 50% compared with the original protein.

The two PEGylated products obtained after purification are further confirmed to be N-terminally monoPEGylated and diPEGylated products, in connection with the experimental results obtained in Example 1. The same result is also obtained through analysis of the peptide mapping of the products modified with PEG having a molecular weight of 30 KDa after trypsinization, indicating that the two products modified with PEG having a molecular weight of 30 KDa are N-terminally monoPEGylated and diPEGylated products.

Example 3: Analysis of PEG-ASP Conjugates and Original Protein by Circular Dichroism Spectroscopy The secondary and tertiary structures of a unPEGylated and PEGylated protein were characterized by circular dichroism spectroscopy. The protein concentrations ranged from 0.1 to 0.2 mg/mL. The sample was charged into a circular dichroism cuvette of 1 mm optical path, and detected for its circular dichroism spectra in a far ultraviolet region (190 nm-250 nm) and a near ultraviolet region (253 nm-480 nm), at a scanning bandwidth of 1 nm and a scanning speed of 500 nm/min. A corresponding buffer was used as the background in each detection, and there measurements were averaged. As can be seen from FIG. 4, the circular dichroism spectrum in the far ultraviolet region of the PEG-ASP conjugate has almost no peak shift as compared with that of the original protein, and no obvious change occurs to the peak value, suggesting that no difference exists in the secondary structure after modification with branched PEG modifiers. This result is in accord with the PEG property. PEG in solution is a flexible amphiphilic polymer, and has no obvious influence on the protein structure after conjugation to the protein surface. Therefore, the PEGylation has no influence on the secondary structure of ASP. Likewise, the circular dichroism spectrum in the near ultraviolet region of the PEG-ASP conjugate has almost no peak shift as compared with that of the original protein, although the peak value varies to some degree, suggesting that PEGylation has no influence on the tertiary structure of ASP. In general, the advanced structure of ASP substantially has no change for the conjugates prepared through site-specific PEGylation. After PEGylation, the structure is unchanged and thus the loss of activity of the conjugate is small compared with activity of the original protein.

Example 4: Analysis of PEG-ASP Conjugates and Original Protein by Fluorescence Spectroscopy The excitation wavelength for intrinsic fluorescence detection of the modified and unmodified protein was 280 nm, and the emission wavelength was in the range of 300-400 nm. The scanning speed was 1200 nm/min. The excitation and emission slit widths were both 5 nm, and the detection was carried out at room temperature by using a 0.1 cm sample cell. The concentration of the protein to be tested was in the range of 0.1-0.2 mg/ml.

The influence of PEGylation on the tertiary structure of asparaginase is detected by intrinsic fluorescence spectroscopy. As shown in FIG. 5, when the excitation wavelength is 280 nm, the asparaginase and PEGylated products thereof emit fluorescence at a peak wavelength of 315 nm. The fluorescence emission spectra of the monoPEGylated and diPEGylated products, and asparaginase are substantially consistent with each other. This suggests that the PEGylation on asparaginase has no influence on the tertiary structure of asparaginase. The emission intensity of PEGylated AEG is slightly lower than that of the unPEGylated protein, which may correlate with the shielding effect of the PEG chain on the emission spectrum of the protein.

Example 5: Pharmacokinetic Study of PEG-ASP Conjugates

The difference between the activities of the PEGylated products of asparaginase modified with branched PEG having a molecular weight of 30 and 40 KDa is not obvious. However, from the perspective of pharmacokinetics, the pharmacokinetic behavior of a product modified with PEG having a high molecular weight is much better. Therefore, in this example, the diPEGylated and monoPEGylated products with branched PEG having a molecular weight of 40 KDa are used for pharmacokinetic study, and compared with the unPEGylated original protein and the commercially available product Pegaspargase.

The pharmacokinetics after administration by intravenous and intramuscular injection were investigated respectively. The sample was labeled with $^{125}I$ by the IODOGEN method, and the labeled sample to be tested was purified. The purity was detected by SHPLC. A series of labeled samples were determined for the protein concentrations by using a BCA Protein Assay Kit, then mixed with an amount of respective unPEGylated samples separately, and diluted with 1× vehicle (by diluting a 10× vehicle to 1× with water for injection), to give a 1.175 mg/mL injectable solution. The radioactivity of about 5 µL of the drug solution was determined. Specific activity=radioactivity/protein concentration. Blood was collected from the rats periodically after administration. If the plasma concentration at the last time point of blood collection in each intravenous administration group was not lower than 1/20 of the plasma concentration determined at the time point of 2 min, blood was continuously collected once a day, until the plasma concentration was lower than 1/20 of the plasma concentration determined at the time point of 2 min. If the plasma concentration at the last time point of blood collection in each intramuscular administration group was not lower than 1/10 of the peak plasma concentration, blood was continuously collected once a day, until the plasma concentration was lower than 1/10 of the peak plasma concentration. After collection, the blood sample was immediately added to an EP tube containing heparin sodium (1000 IU/mL, 10 µL) as an anticoagulant, inverted 5-10 times, and centrifuged for 5 min at 4000 rpm, to separate the plasma. 50 µL of the plasma was added with equal volume of 20% trichloroacetic acid (TCA), fully mixed by vortex, and determined for the total radioactivity. Subsequently, the system was centrifuged for 10 min at 4500 rpm and normal temperature. The supernatant was discarded, and the radioactivity of the pellet was determined.

Calculation of pharmacokinetic parameters: Main pharmacokinetic parameters including AUC were calculated by non-compartmental analysis (NCA) using WinNonlin6.2;

2) Concentration calculation:

$$\text{Drug content} = \frac{\text{Radioactivity of sample}}{\text{Specific activity of protein}} \Big/ \text{Volume (weight) of sample};$$

3) Data processing: The mean and standard deviation were statistically calculated by Excel 2007.

The calculation results of the pharmacokinetic parameters are shown in Tables 2 and 3 and FIGS. 6a and 6b.

TABLE 2

Pharmacokinetic parameters of PEG-ASP conjugates vs asparaginase (intravenous injection)

| Sample | T½ (h) | AUC (mg/L*h) | CL (L/h/kg) |
|---|---|---|---|
| Asparaginase | 2.84 | 123896.00 | 18.50 |
| Pegaspargase | 53.41 | 3738733.50 | 0.60 |
| Y-PALD-40K-ASP (Mono) | 34.38 | 1701512.23 | 1.35 |
| Y-PALD-40K-ASP (Di) | 58.70 | 3827982.37 | 0.59 |

TABLE 3

Pharmacokinetic parameters of PEG-ASP conjugates vs asparaginase (intramuscular injection)

| Sample | T½ (h) | AUC (mg/L*h) | CL (L/h/kg) |
|---|---|---|---|
| Asparaginase | 6.97 | 55241.11 | 32.06 |
| Pegaspargase | 42.62 | 3046417.50 | 0.75 |
| Y-PALD-40K-ASP (Mono) | 37.22 | 1008025.72 | 2.25 |
| Y-PALD-40K-ASP (Di) | 56.00 | 3367604.25 | 0.69 |

Compared with asparaginase, the half-life of Y-PALD-40K-ASP (Mono) and Y-PALD-40K-ASP (Di) is obviously extended in both case of intravenous injection and intramuscular injection, and the area under curve (AUC) after administration is significantly increased. Moreover, the clearance rate of Y-PALD-40K-ASP (Mono) and Y-PALD-40K-ASP (Di) in blood is also far lower than that of asparaginase. It can be seen that compared with asparaginase, the in-vivo stability of Y-PALD-40K-ASP (Mono) and Y-PALD-40K-ASP (Di) is increased to some degree. The increase in the in-vivo stability of Y-PALD-40K-ASP (Di) is more obvious, and thus the half life is considerably increased, the metabolic rate in blood is greatly reduced, and the duration of action of the drug is effectively extended, as shown in FIGS. 6a and 6b. As can be seen from the pharmacokinetic parameters calculated by software, compared with commercially available Pegaspargase, the half-life of Y-PALD-40K-ASP (Di) in both case of intravenous injection and intramuscular injection is higher than that of Pegaspargase.

Example 6: Stability Study of PEG-ASP Conjugates

Pegaspargase, Oncaspar (available from Sigma-Tau Pharmaceuticals, Inc.), and Y-PALD-40K-ASP (Di) were diluted to 1 mg/ml with a Tris-HCl buffer (pH 9.0), and placed in water bath at 55° C. 100 μl was removed at 0, 1, 2, 3, 4, and 5 hrs, for detecting the enzyme activity. The activity determination result is shown in FIG. 7.

It can be seen from FIG. 7 that after 1 hr treatment in the water bath, the activity of Pegaspargase is substantially completely lost, and is almost zero; the enzyme activity of the Oncaspar sample is slightly higher than that of Pegaspargase, and about 30% of the activity is retained after 1 hr treatment; and in contrast, the Y-PALD-40K-ASP (Di) sample retains about 80% of the activity after 1 hr treatment, and still retains about 60% of the bioactivity after 5 hr treatment, so that the stability is significantly advantageous over that of Pegaspargase and Oncaspar. The significant decrease in the activity of Pegaspargase and Oncaspar may be attributed to the easy detachment of PEG. Due to the persistent detachment of PEG molecules, the protection of PEG for asparaginase is greatly reduced, causing a high activity loss. No detachment of PEG takes place during the treatment of the Y-PALD-40K-ASP (Di) sample, and PEG molecules can better improve the thermal stability of asparaginase, so the activity loss is relatively slow.

Example 7: In-Vitro Activity Detection of PEG-ASP Conjugates

The amido group on asparagine can be hydrolyzed by L-asparaginase. Based on this principle, the activity of asparaginase was determined. The specific determination method was as described in *Pharmacopoeia of People's Republic of China* (2005 Edition), Part II, Page 31. The reagents needed were all available from Sinopharm Group Chemical Reagent Co., Ltd. The detected samples were respectively Y-PALD-40K-ASP (Mono), Y-PALD-40K-ASP (Di), Y-PALD-30K-ASP (Mono), Y-PALD-30K-ASP (Di) and unPEGylated original protein as well as similar product Pegaspargase (manufactured by Jiangsu Hengrui Pharmaceutical Co., Limited) and Oncaspar (manufactured by Sigma-Tau Pharmaceuticals, Inc.) available in the market. The comparison result of their relative activities is shown in FIG. 8.

It can be seen from the activity determination result of FIG. 8 that the activities of the PEGylated asparaginase according to the present invention and the commercially available similar products Pegaspargase and Oncaspar are all decreased to some degree. However, Y-PALD-40K-ASP (Mono), Y-PALD-40K-ASP (Di), Y-PALD-30K-ASP (Mono), and Y-PALD-30K-ASP (Di) retain 90.25%, 90.5%, 89.5%, and 85.8% of the activity of the original protein respectively, and Pegaspargase and Oncaspar retain only 62.9% and 53.5% of the activity of the original protein.

It can be seen from the enzyme activity determination result that the site-specific PEGylated product of asparaginase prepared in Example 1 of the present invention has an activity that is significant higher than the activity of the commercially available products Pegaspargase and Oncaspar. The commercially available Pegaspargase and Oncaspar are products obtained by random modification with PEG having a molecular weight of 5000 Da, and the PEGylated asparaginase retains only 62.9% and 53.5% of the activity of the original protein. In the present invention, N-terminal site-specific modification is made to asparaginase with 30-40 kDa PEG-propionaldehyde, and the PEGylated asparaginase retains about 90% of the bioactivity of the original protein. Moreover, based on a common rule existing in PEGylation, when the same type of PEG is used for protein modification, the loss in activity of the PEGylated protein increases with increasing molecular weight of PEG. However, unexpectedly no such a rule is found for the PEGylated products prepared in the present invention, since the activity of the PEGylated products is higher than that of Pegaspargase, and also the PEGylated products with a PEG modifier having a molecular weight of 30 and 40 KDa provided in the present invention retain about 90% of the activity of the original protein, where the activity of the PEGylated products with 40 KDa PEG is slightly higher than that of the PEGylated products with 30 KDa PEG. Furthermore, for the PEGylated products with a PEG modifier of the same molecular weight, one more PEG molecule is coupled to each asparaginase molecule in the diPEGylated product, compared with a monoPEGylated product. Therefore, the molecular weight of the diPEGylated product is obviously higher than that of the monoPEGylated product. This can also be seen from the gel filtration analysis profile of Example 1. Accordingly, based on the common rule existing in PEGylation, the activity of the diPEGylated product should be greatly lower than that of the monoPEGylated product. However, essentially no difference exists between the activity of the monoPEGylated product and the diPEGylated product prepared in the present invention. This may correlates closely with the structural features of asparaginase. Asparaginase is a polymeric protein formed with 4 subunits, in which the 4 subunits have fully identical amino acid sequence, and the active center is in the space surrounded by 4 subunits. In the prepared diPEGylated product, the PEG molecule is coupled respectively to the N terminus of 2 non-adjacent subunits, and thus the two PEG molecules are relatively independent and cause no large steric hindrance to each other. Therefore, there is no obvious difference between the activity of the monoPEGylated and diPEGylated product.

Furthermore, examples of N-terminal site-specific PEGylation of asparaginase are reported in existing literatures or patent documents, where linear PEG is used, and the prepared PEGylated products are N-terminal site-specific monoPEGylated products that retain only about 40% of the activity of the original protein, which is far below the activity of the PEGylated products prepared in the present invention. Since in these examples, the N-terminal site-specific PEGylation is carried out with low-molecular-weight PEG in each case, the activity of the PEGylated products is theoretically higher than that of the present invention. However, unexpectedly the PEGylated products prepared in the present invention have a higher activity. Therefore, it can be seen that although there are some common rules to follow in the development of long-acting protein drugs by protein PEGylation, it is most important to carry out lots of optimizations and screenings in connection with the structural features of the modified protein drugs, so as to prepare a most desirable modified product. This is a process depending on specific conditions.

Example 8: Evaluation of Inhibition of PEG-ASP Conjugates on Tumor Cells

To evaluate the inhibition of PEG-ASP conjugates on tumor cells, and compare with that of Pegaspargase and Oncaspar, THP-1 (derived from human monocytic leukemia cell line), Raji (derived from human lymphoma cell line), and L1210 (derived from mouse leukemia cell) were used for evaluation. The inhibition on cells was tested by the MTT method, and the inhibition rate at different concentrations was investigated, to finally calculate the $IC_{50}$ value. The calculation results are shown in Table 4 below.

TABLE 4

IC50 values of various PEG-ASP conjugates and Pegaspargase for tumor cells

| Tumor cell | ASP | Pegaspargase | Oncaspar | Y-PALD-40K-A SP (Mono) | Y-PALD-40K-A SP (Di) |
| --- | --- | --- | --- | --- | --- |
| THP-1 | 3.8 μmol/L | 7.9 μmol/L | 7.5 μmol/L | 2.05 μmol/L | 1.93 μmol/L |
| Raji | 8.9 μmol/L | 8.8 μmol/L | 8.1 μmol/L | 2.7 μmol/L | 2.6 μmol/L |
| L1210 | 7.9 μmol/L | 10.28 μmol/L | 10.69 μmol/L | 3.75 μmol/L | 3.05 μmol/L |

As can be known from the experimental result, the site-specific PEGylated asparaginase has a killing effect for the above 3 tumor cells that is generally higher than that of the unmodified asparaginase and an anti-tumor activity that is obviously higher than that of Pegaspargase and Oncaspar, and exhibits a good anti-tumor effect on numerous cell lines. Therefore, the site-specific PEGylated products of asparaginase prepared in the present invention has better inhibition on tumor cells due to the higher specific activity than that of Pegaspargase and Oncaspar.

What is claimed is:

1. A site-specific di-polyethylene glycolylated (diPEGylated) L-asparaginase or a pharmaceutically acceptable salt or complex thereof, wherein each of N-terminal aminos of 2 out of 4 subunits of the diPEGylated L-asparaginase is coupled to one polyethylene glycol (PEG) molecule separately, wherein the PEG molecule prior to coupling to the L-asparaginase is branched and has a molecular weight of 30-40 KDa, and has the general structural formula below:

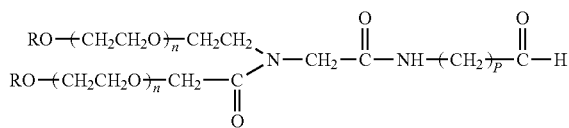

wherein R is H or a C1-C4 alkyl, n is an integer from 320 to 455, P is an integer from 1 to 4.

2. The site-specific diPEGylated L-asparaginase or pharmaceutically acceptable salt or complex thereof according to claim 1, wherein the aldehyde group is acetaldehyde, propionaldehyde, butyraldehyde, or valeraldehyde.

3. The site-specific diPEGylated L-asparaginase or pharmaceutically acceptable salt or complex thereof according to claim 2, wherein R is methyl, and P is 2.

4. A method for preparing the site-specific diPEGylated L-asparaginase or pharmaceutically acceptable salt or complex thereof according to claim 1, comprising:
   step 1: formulating a 15-20 mg/mL L-asparaginase solution in 40 mM acetic acid-sodium acetate buffer pH 5.0;
   step 2: reacting for 12-24 hours at 4° C. at a molar ratio of L-asparaginase:PEG:reducing agent=1:(4-5):(100-200); and
   step 3: purifying by ion exchange chromatography after reaction, to finally obtain the diPEGylated L-asparaginase according to claim 1, wherein the reducing agent is sodium cyanoborohydride, and
wherein the PEG of step 2 has the general structural formula below:

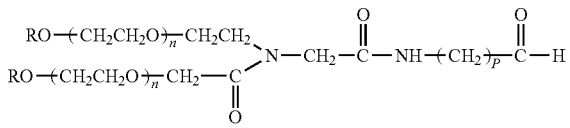

wherein R is H or a C1-C4 alkyl, n is an integer from 320 to 455, and P is an integer from 1 to 4.

5. A pharmaceutical composition, comprising the site-specific diPEGylated L-asparaginase or pharmaceutically acceptable salt or complex thereof according to claim 1, and a pharmaceutically acceptable adjuvant.

6. The pharmaceutical composition according to claim 5, which is in the dosage form of a freeze-dried powder injection.

7. A method for treating tumors in a patient in need thereof which comprises administering to said patient a therapeutically effective amount of the site-specific diPEGylated L-asparaginase or pharmaceutically acceptable salt or complex thereof according to claim 1.

8. The method according to claim 7, wherein the tumors include acute lymphoblastic leukemia (ALL) tumors, NK/T cell lymphoma tumors, Hodgkin's disease tumors, acute myeloid leukemia tumors, acute myelomonocytic leukemia tumors, chronic lymphocytic leukemia, lymphosarcoma tumors, reticulum cell sarcoma tumors, or melanotic sarcoma tumors.

9. A method for treating tumors in a patient in need thereof which comprises administering to said patient a therapeutically effective amount of the pharmaceutical composition according to claim 5.

10. The method according to claim 9, wherein the tumors include acute lymphoblastic leukemia (ALL) tumors, NK/T cell lymphoma tumors, Hodgkin's disease tumors, acute myeloid leukemia tumors, acute myelomonocytic leukemia tumors, chronic lymphocytic leukemia tumors, lymphosarcoma tumors, reticulum cell sarcoma tumors, or melanotic sarcoma tumors.

\* \* \* \* \*

SEQUENCE LISTING

```
<160> NUMBER OF SEQ ID NOS: 1

<210> SEQ ID NO 1
<211> LENGTH: 348
<212> TYPE: PRT
<213> ORGANISM: Escherichia coli
<220> FEATURE:
<221> NAME/KEY: misc_feature
<223> OTHER INFORMATION: Escherichia coli EC 3.5.1.1

<400> SEQUENCE: 1

Met Glu Phe Phe Lys Lys Thr Ala Leu Ala Ala Leu Val Met Gly Phe
1               5                   10                  15

Ser Gly Ala Ala Leu Ala Leu Pro Asn Ile Thr Ile Leu Ala Thr Gly
                20                  25                  30

Gly Thr Ile Ala Gly Gly Gly Asp Ser Ala Thr Lys Ser Asn Tyr Thr
            35                  40                  45

Val Gly Lys Val Gly Val Glu Asn Leu Val Asn Ala Val Pro Gln Leu
        50                  55                  60

Lys Asp Ile Ala Asn Val Lys Gly Glu Gln Val Val Asn Ile Gly Ser
65                  70                  75                  80

Gln Asp Met Asn Asp Asn Val Trp Leu Thr Leu Ala Lys Lys Ile Asn
                85                  90                  95

Thr Asp Cys Asp Lys Thr Asp Gly Phe Val Ile Thr His Gly Thr Asp
            100                 105                 110

Thr Met Glu Glu Thr Ala Tyr Phe Leu Asp Leu Thr Val Lys Cys Asp
        115                 120                 125

Lys Pro Val Val Met Val Gly Ala Met Arg Pro Ser Thr Ser Met Ser
    130                 135                 140

Ala Asp Gly Pro Phe Asn Leu Tyr Asn Ala Val Val Thr Ala Ala Asp
145                 150                 155                 160

Lys Ala Ser Ala Asn Arg Gly Val Leu Val Val Met Asn Asp Thr Val
                165                 170                 175
```

```
Leu Asp Gly Arg Asp Val Thr Lys Thr Asn Thr Thr Asp Val Ala Thr
            180                 185                 190

Phe Lys Ser Val Asn Tyr Gly Pro Leu Gly Tyr Ile His Asn Gly Lys
        195                 200                 205

Ile Asp Tyr Gln Arg Thr Pro Ala Arg Lys His Thr Ser Asp Thr Pro
        210                 215                 220

Phe Asp Val Ser Lys Leu Asn Glu Leu Pro Lys Val Gly Ile Val Tyr
225                 230                 235                 240

Asn Tyr Ala Asn Ala Ser Asp Leu Pro Ala Lys Ala Leu Val Asp Ala
                245                 250                 255

Gly Tyr Asp Gly Ile Val Ser Ala Gly Val Gly Asn Gly Asn Leu Tyr
            260                 265                 270

Lys Ser Val Phe Asp Thr Leu Ala Thr Ala Ala Lys Thr Gly Thr Ala
            275                 280                 285

Val Val Arg Ser Ser Arg Val Pro Thr Gly Ala Thr Thr Gln Asp Ala
        290                 295                 300

Glu Val Asp Asp Ala Lys Tyr Gly Phe Val Ala Ser Gly Thr Leu Asn
305                 310                 315                 320

Pro Gln Lys Ala Arg Val Leu Leu Gln Leu Ala Leu Thr Gln Thr Lys
                325                 330                 335

Asp Pro Gln Gln Ile Gln Gln Ile Phe Asn Gln Tyr
            340                 345
```